United States Patent
Shin et al.

(10) Patent No.: US 11,566,221 B2
(45) Date of Patent: Jan. 31, 2023

(54) METHODS OF DIFFERENTIATION TO NEURONAL CELLS AND KITS THEREFOR

(71) Applicant: LIFE TECHNOLOGIES CORPORATION, Carlsbad, CA (US)

(72) Inventors: Soojung Shin, Clarksburg, MD (US); Yiping Yan, Clarksburg, MD (US); Daniel Beacham, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 715 days.

(21) Appl. No.: 16/344,497

(22) PCT Filed: Oct. 20, 2017

(86) PCT No.: PCT/US2017/057641
§ 371 (c)(1),
(2) Date: Apr. 24, 2019

(87) PCT Pub. No.: WO2018/080925
PCT Pub. Date: May 3, 2018

(65) Prior Publication Data
US 2019/0241869 A1    Aug. 8, 2019

Related U.S. Application Data

(60) Provisional application No. 62/412,014, filed on Oct. 24, 2016.

(51) Int. Cl.
| | |
|---|---|
| *C12N 5/0793* | (2010.01) |
| *C12N 5/00* | (2006.01) |
| *C12N 5/0735* | (2010.01) |
| *C12N 5/074* | (2010.01) |

(52) U.S. Cl.
CPC ......... *C12N 5/0619* (2013.01); *C12N 5/0031* (2013.01); *C12N 5/0037* (2013.01); *C12N 5/0606* (2013.01); *C12N 5/0696* (2013.01); *C12N 2500/99* (2013.01); *C12N 2501/42* (2013.01); *C12N 2506/08* (2013.01)

(58) Field of Classification Search
CPC ................ C12N 5/0618; C12N 5/0031; C12N 2500/99; C12N 2501/42
See application file for complete search history.

(56) References Cited

U.S. PATENT DOCUMENTS

| | | |
|---|---|---|
| 2014/0248696 A1 | 9/2014 | Zhang et al. |
| 2016/0152950 A1 | 6/2016 | Zhang et al. |

FOREIGN PATENT DOCUMENTS

| | | |
|---|---|---|
| WO | WO-2010014990 A2 | 2/1920 |
| WO | WO-2004015077 A2 | 2/2004 |
| WO | WO-2009122413 A1 | 10/2009 |
| WO | WO-2014127289 A1 | 8/2014 |
| WO | WO-2014153230 A1 | 9/2014 |
| WO | WO-2016012570 A1 | 1/2016 |

OTHER PUBLICATIONS

Wong (Jour Biol Chem, 2004, 279:12876-12882).*
Ogura (2013, Stem Cells and Development, 22:374-382).*
Cai (Zhonghua yi xue za zhi, Feb. 1, 2008, 88(7):480-483, English summary attached).*
Yuen (2005, The Journal of Neuroscience, 115:5488-5501).*
Venere (Development, 2012, 139:3938-3949).*
International Search Report and Written Opinion for Application No. PCT/US2017/057641, dated Dec. 13, 2017, 12 pages.
Lodovica Borghese et al: "Inhibition of Notch Signaling in Human Embryonic Stem Cell-Derived Neural Stem Cells Delays G1/S Phase Transistion and Accelerates Neuronal Differentiation In Vivo and In Vitro", Stem Cells, vol. 28, No. 5, May 10, 2010 (May 10, 2010), pp. 955-964, XP055128372, ISSN: 1066-5099, DOI: 10.1002/stem.408.
W. Li et al: "Rapid induction and long-term self-renewal of primitive neural precursors from human embryonic stem cells by small molecule inhibitors", Proceedings of the National Academy of Sciences, vol. 108, No. 20, Apr. 27, 2011 (Apr. 27, 2011), pp. 8299-8304, XP055098564, ISSN: 0027-8424, DOI: 10.1073/pnas.1014041108.

* cited by examiner

*Primary Examiner* — Valarie E Bertoglio

(57) ABSTRACT

Embodiments herein provide methods of differentiating neural stem cells to neuronal cells while concomitantly retarding neural stem cell proliferation. Resultant cultures demonstrate reduced clumping of cells, increased purity of neuronal cells and accelerated electrophysiology as compared to control methods.

12 Claims, 13 Drawing Sheets

WITHOUT COMPOUND E   WITH COMPOUND E

WITHOUT COMPOUND E

DAPI

WITH COMPOUND E

DAPI

NESTIN

NESTIN

DCX

DCX

WITHOUT COMPOUND E

WITH COMPOUND E

DAPI

DAPI

NESTIN

NESTIN

DCX

DCX

WITHOUT GAMMA SECRETASE INHIBITOR TREATMEMT

WITH GAMMA SECRETASE INHIBITOR TREATMEMT

MAP 2

MAP 2

SOX 1

SOX 1

WITHOUT GAMMA SECRETASE INHIBITOR TREATMEMT

EdU

WITH GAMMA SECRETASE INHIBITOR TREATMEMT

EdU

CAPSASE 9

CAPSASE 9

WITHOUT GAMMA SECRETASE INHIBITOR TREATMEMT

WITH GAMMA SECRETASE INHIBITOR TREATMEMT

WITHOUT GAMMA SECRETASE INHIBITOR TREATMEMT

GFAP

WITH GAMMA SECRETASE INHIBITOR TREATMEMT

GFAP

Hu C & Hu D

Hu C & Hu D

METHODS OF DIFFERENTIATION TO NEURONAL CELLS AND KITS THEREFOR

CROSS-REFERENCE TO RELATED APPLICATIONS

This application is a 371 of International Application No. PCT/US2017/057641, filed Oct. 20, 2017, and claims benefit of priority to U.S. Provisional Application No. 62/412,014, filed Oct. 24, 2016, which disclosures are herein incorporated by reference in their entirety.

FIELD

Present embodiments relate to retarding proliferation of multipotent neural stem cells and concomitantly differentiating to neuronal cells, as well as differentiating primary cortical neurons and concomitantly retarding glial cell proliferation, methods, kits and uses therefor.

INTRODUCTION

Neuronal cells differentiated from human pluripotent stem cell (hPSC)-derived neural stem cells (NSCs) are used to model the physiology of neurons and neurological diseases in vitro. When hPSCs are induced in vitro into neural stem cells (NSCs), and the NSCs then differentiated in vitro into neuronal cells, undifferentiated NSC's readily take over the culture because they proliferate faster than the maturing neuronal cells. Unchecked proliferation of undifferentiated NSCs results in increased cell density and resultant cell clumping. Impure neuronal cultures and cell clumps increase the difficulty of long-term maintenance of cultured neuronal cells as well as downstream analyses such as cell counting, cell imaging, and cell assays, for example.

Primary neuronal cells differentiated from neural progenitors isolated from rodent embryonic brain provide a classical cell model to study functions of neuronal cells in vitro because isolated neural progenitors from rodent embryonic brain contain both neuronal and glial progenitors. In the differentiation of primary neuronal cells, the number of glial cells increases during the period of prolonged differentiation because of the proliferative property of glial progenitors. For researchers to use pure neuronal cells for their studies, contaminating glial cells present a problem that has been addressed in the past by culturing primary neuronal cultures for several days with anti-mitotics such as fluorodeoxyuridine (FDU) and/or cytosine arabinofuranoside (Ara-C) that kills all proliferating cells by disturbing DNA synthesis. However, these mitotics are also toxic to neuronal cells.

Embodiments herein address these problems and provide solutions that have unexpected benefits.

SUMMARY

In one aspect, embodiments herein address the problem of unchecked proliferation of neural stem cells during differentiation to neuronal cells and provide methods and kits that solve the problem with the unexpected benefits of reduced clumping during differentiation, and enhanced electrophysiology of resultant neuronal cells. In one aspect, cultures resulting from the methods herein, as compared to cultures not treated as described herein, have at least one of the following attributes: greater than 50% of the cells are neuronal cells, greater than 50% of the cells are MAP2 positive cells, greater than 50% of the cells are HuC/D positive cells, cells have average or better than average neurite length, cells have equivalent or better electrical activity, cells have accelerated excitability in response to a stimulus, and greater than 50% of the cells test negative for the SOX 1 marker at Day 14 of differentiation.

In another aspect, embodiments herein address the problem of unchecked proliferation of glial progenitors during differentiation to neuronal cells and provide methods and kits for virtually eliminating glial progenitors.

In some embodiments, a method for accelerating differentiation of at least one neural stem cell to at least one neuronal cell and concomitantly retarding neural stem cell proliferation is provided, the method comprising, culturing the at least one neural stem cell in a differentiation medium for a time and under conditions to form the at least one neuronal cell, wherein the differentiation medium comprises a serum-free neural stem cell culture medium, and a serum-free supplement comprising at least one gamma secretase inhibitor, wherein excitability of the at least one neuronal cell is accelerated as compared to culturing the at least one neural stem cell in the differentiation medium lacking the at least one gamma secretase inhibitor. In an embodiment, excitability of the at least one neuronal cell when differentiated in the presence of a gamma secretase inhibitor is accelerated by greater than 100% compared to a baseline value at Day 7. In that embodiment, the control culture differentiated without presence of the gamma secretase inhibitor was measured at a 37% increase in excitability compared to a baseline value on Day 7.

A method of reducing cell clumping during differentiation of neural stem cells to neuronal cells is an aspect of embodiments herein, the method comprising, culturing the neural stem cells in a differentiation medium for a time and under conditions to form neuronal cells, wherein the differentiation medium comprises a serum-free neural stem cell culture medium, and a serum-free supplement comprising at least one gamma secretase inhibitor, wherein cell clumping is reduced at least 50% when compared to culturing the neural stem cells in the differentiation medium lacking the at least one gamma secretase inhibitor. In one embodiment, cell clumping is reduced at least 75%, or in another embodiment, reduced at least 90%, when compared to culturing in the absence of the at least one gamma secretase inhibitor at Day 14 of differentiation.

A method of differentiation of primary cells to Hu C & Hu D positive neuronal cells and concomitantly retarding differentiation of the primary cells to GFAP positive astrocytes is a further embodiment herein, the method comprising, culturing the primary cells in a differentiation medium for a time and under conditions to form Hu C & Hu D positive neuronal cells, wherein the differentiation medium comprises at least one serum-free neural stem cell culture medium, and a serum-free supplement comprising at least one gamma secretase inhibitor, wherein differentiation of the primary cells to GFAP positive astrocytes is reduced when compared to culturing the primary cells in the differentiation medium lacking the at least one gamma secretase inhibitor. In an embodiment, the reduction in GFAP positive astrocytes is at least 50% as compared to culturing in the differentiation medium lacking the at least one gamma secretase inhibitor.

In some aspects of the above described methods, the serum-free supplement of the differentiation medium comprises a gamma secretase inhibitor selected from the group consisting of Compound E, YO-01027, LY411575, MK-0752, a salt thereof, and a combination thereof. In another embodiment, the serum-free supplement comprises a gamma secretase inhibitor selected from the group consisting of Compound E. YO-01027. LY411575, a salt thereof, and a combination thereof. In another aspect of the above described methods, the serum-free supplement of the differentiation medium comprises a gamma secretase inhibitor selected from the group consisting of Compound E, YO-01027, a salt thereof, and a combination thereof. In another aspect of the above described methods, the serum-free supplement of the differentiation medium comprises the gamma secretase inhibitor YO-01027, or a salt thereof. In another aspect of the above described methods, the serum-free supplement of the differentiation medium comprises the gamma secretase inhibitor Compound E, or a salt thereof.

In another aspect, the gamma secretase inhibitor is present in the differentiation medium at a concentration of 0.1 micromolar to 80 micromolar, 0.1 micromolar to 40 micromolar, a concentration of 0.1 micromolar to 20 micromolar, a concentration of 0.2 micromolar to 10 micromolar, a concentration of 0.2 micromolar to 2.0 micromolar, a concentration of 0.2 to 1.0 micromolar, or a concentration of 0.2 to 0.5 micromolar.

The at least one neural stem cell of the above described method is derived from an induced human pluripotent stem cell, or alternatively, the at least one neural stem cell is derived from a human embryonic stem cell.

In some embodiments, the at least one neural stem cell is a SOX1 positive neural stem cell, a SOX2 positive neural stem cell, and/or a NESTIN positive neural stem cell, and the neuronal cell is a MAP2 positive neuronal cell, a DCX positive neuronal cell and/or a HU C&D positive neuronal cell.

In some aspects of method embodiments, the at least one neuronal cell is maintained in culture for at least a period of five weeks.

A kit for accelerating differentiation of at least one neural stem cell to at least one neuronal cell and concomitantly retarding neural stem cell proliferation is a further embodiment herein, the kit comprising, at least one serum-free neural stem cell culture medium, and a serum-free supplement comprising at least one gamma secretase inhibitor, and optionally, reagents and instructions pertaining to use of the kit. In some embodiments, the serum-free supplement of the kit comprises a gamma secretase inhibitor selected from the group consisting of Compound E, YO-01027, LY411575, MK-0752, a salt thereof, and a combination thereof. In some aspects, the serum-free supplement of the kit comprises a gamma secretase inhibitor selected from the group consisting of Compound E, YO-01027, and LY411575, a salt thereof, and a combination thereof. In an embodiment, the serum-free supplement has a 100× concentration such that, e.g., 5 mL of the 100× concentration is added to the serum-free neural stem cell culture medium to form the differentiation medium.

A method of treating a subject having a neurodegenerative condition is an aspect herein, the method comprising administering to the subject a pharmaceutical composition comprising neuronal cells made by any one of the methods described above. In one aspect, the neuronal cells are derived from a neural stem cell autologous for the subject and differentiation is ex vivo prior to administration, e.g., by transplantation. In another aspect, the neuronal cells are derived from a neural stem cell allogeneic for the subject and differentiation is ex vivo prior to administration, e.g., by transplantation. The neurodegenerative condition may be, e.g., Parkinson's disease. Huntington's disease, stroke effects, or dementia such as Alzheimer's conditions.

DRAWINGS

The skilled artisan will understand that the drawings, described below, are for illustration purposes only. The drawings are not intended to limit the scope of the present teachings in any way.

FIG. 1A-FIG. 1B provide phase-contrast images of cells without (FIG. 1A) and with (FIG. 1B) the presence of Compound E at Day 5 of neuronal differentiation. Note the neurite outgrowth of cells differentiated in the presence of Compound E.

FIG. 1C-FIG. 1H provide immunofluorescent images of cells at Day 7 of differentiation without Compound E (left column) and with Compound E (right column). DAPI is a nuclear stain, NESTIN is a stain for neural stem cells and DCX is a stain for neuronal cells.

FIG. 1I-FIG. 1N provide immunofluorescent images of cells at Day 14 of differentiation without Compound E (left column) and with Compound E (right column). DAPI is a nuclear stain, NESTIN is a stain for neural stem cells and DCX is a stain for neuronal cells.

FIG. 2A-FIG. 2F provide images at Day 14 of neuronal differentiation of H9 human ESC-derived NSCs without (first column) or with (second column) the presence of Compound E during differentiation.

FIG. 2A provides a phase-contrast image of cells without the presence of Compound E during neuronal differentiation that shows cell clump formation. Compare this image with the phase-contrast image of cells differentiated in the presence of Compound E in FIG. 2B. Evenly distributed cells are evident without formation of cell clumps. FIG. 2C provides an immunofluorescent image of cells differentiated without Compound E and stained with antibodies against the neuronal marker MAP2. Compare this image with the image of FIG. 2D that shows cells differentiated in the presence of Compound E stained with antibodies against the neuronal marker MAP2. FIG. 2E provides an immunofluorescent image of cells differentiated without Compound E and stained with antibodies against the neural stem cell marker SOX1. Compare this image with the image of FIG. 2F that shows cells differentiated in the presence of Compound E stained with antibodies against the neural stem cell marker SOX1.

FIG. 3 provides a quantitative measure of the degree of cell clumping after two weeks of culture in the differentiation medium without and with the presence of Compound E. A 90% reduction in clumping is found when Compound E is present in the differentiation medium.

FIG. 4A and FIG. 4B provide images that assess proliferation of cells at six days of differentiation without (FIG. 4A) and with (FIG. 4B) Compound E.

FIG. 4C and FIG. 4D provide images that assess apoptotic cell death at six days of differentiation without (FIG. 4C) and with (FIG. 4D) Compound E.

FIG. 5A and FIG. 5B provide quantitative analyses of the data of FIG. 4A-FIG. 4D. FIG. 5A demonstrates that proliferation of neural stem cells is substantially arrested in the presence of Compound E and FIG. 5B shows that no significant amount of cell death has occurred in either the absence or the presence of Compound E.

FIG. 6 provides data to compare the effect of a number of gamma secretase inhibitors on cell clumping during differentiation in the absence and the presence of the inhibitor. Various concentrations of the inhibitors were studied ranging from 0.01 micromolar to 160 micromolar. See Example 4 for the concentrations of inhibitors used to generate the data of this figure. The double asterisks show the statistical analyses as carried out by the All Pairs Tukey-Kramer analyses with a p value less than 0.01.

Figure 9A:
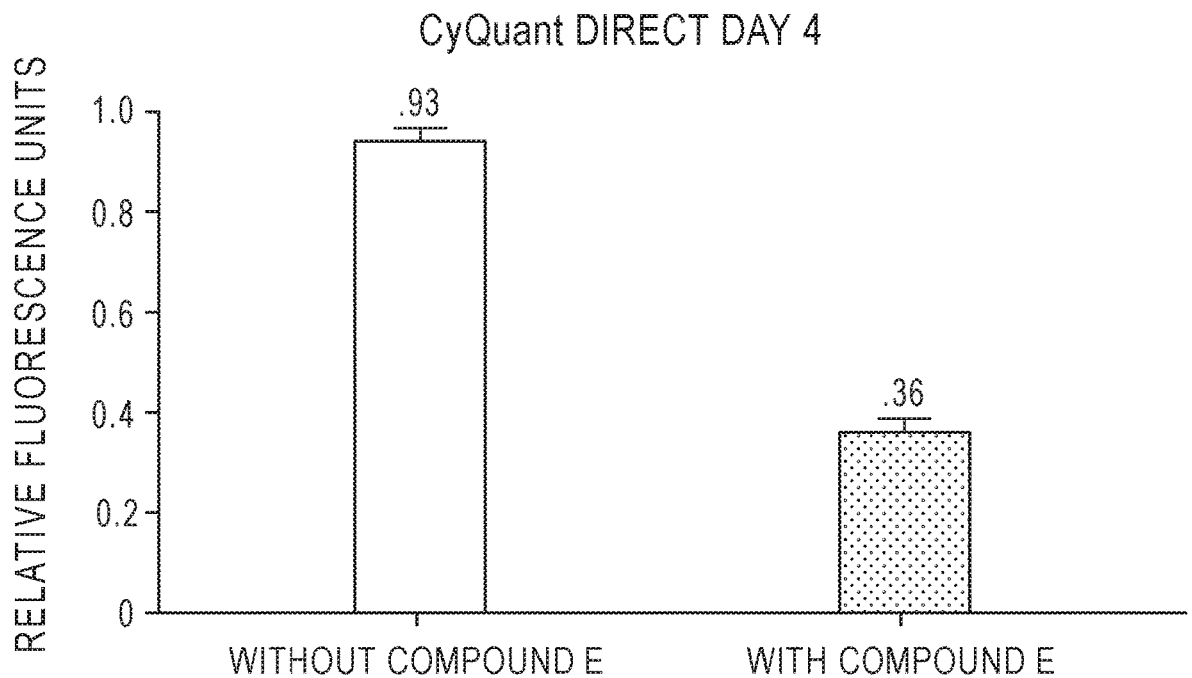
Figure 9B:
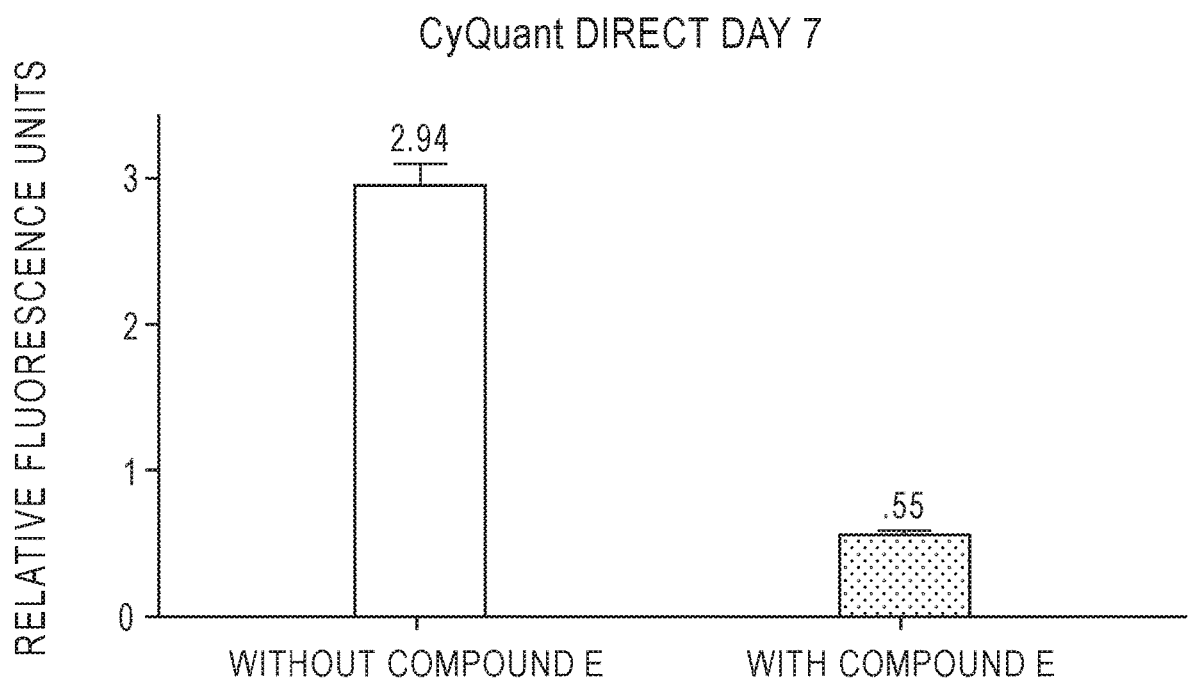

FIG. 9A and FIG. 9B provide measurements of cell proliferation of control NSC cultures (n=8) compared to cultures differentiated in the presence of Compound E to neuronal cells (n=7) on Day 4 (FIG. 9A) and on Day 7 (FIG. 9B) using the CYQUANT™ Direct Cell Proliferation Assay as described in Example 7.

Figure 9C:
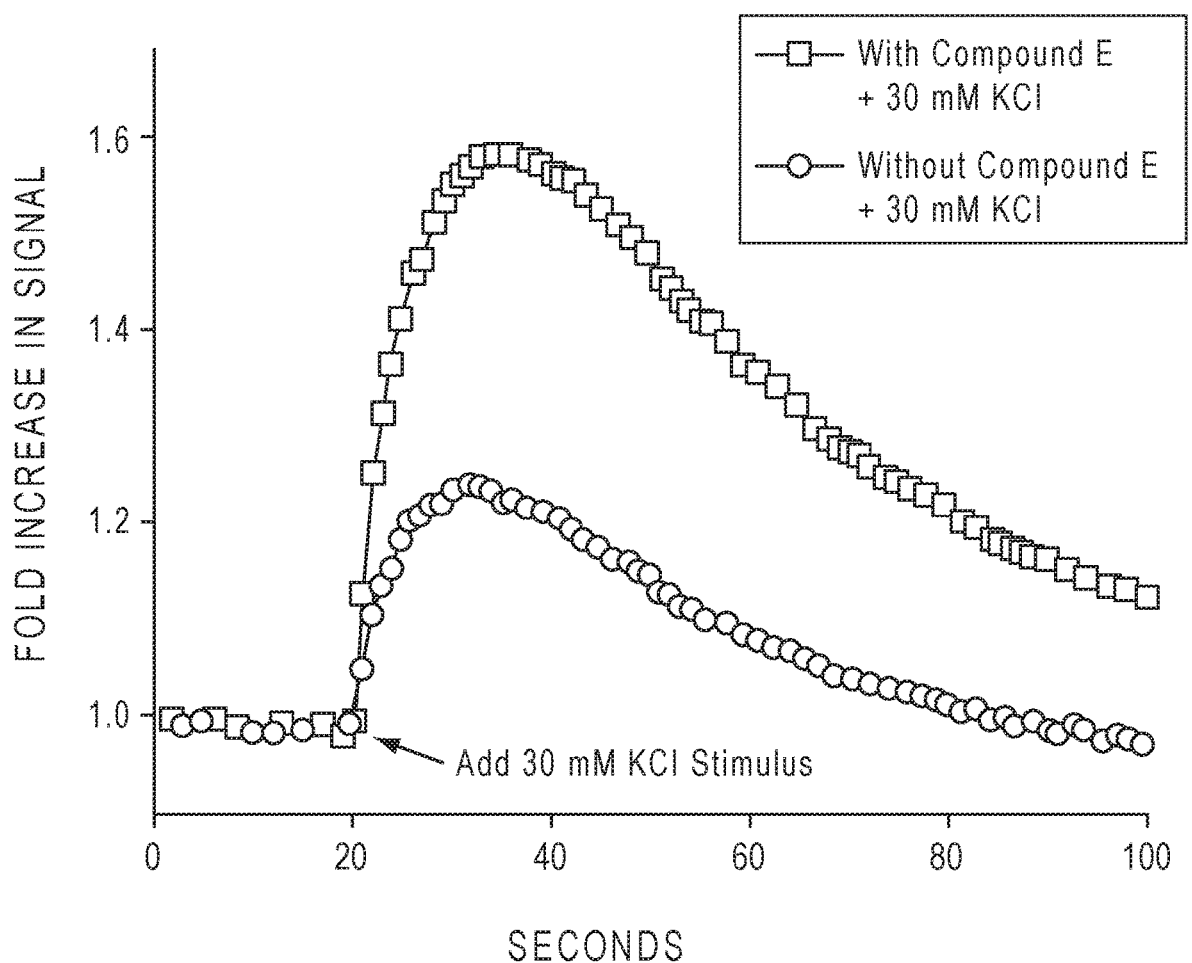

FIG. 9C provides a plot of signal vs time for measuring calcium flux using the Fluo-4 Calcium Imaging Kit. Representative traces of fluorescent response to the addition of the 30 mM KCl stimulus to control NSC cultures and to cultures differentiated in the presence of Compound E to neuronal cells are provided. The signal is measured at 1 hZ and plotted in a running average of multiple wells as fold increase, designated as (signal max−signal min)/signal min.

Figure 10A:
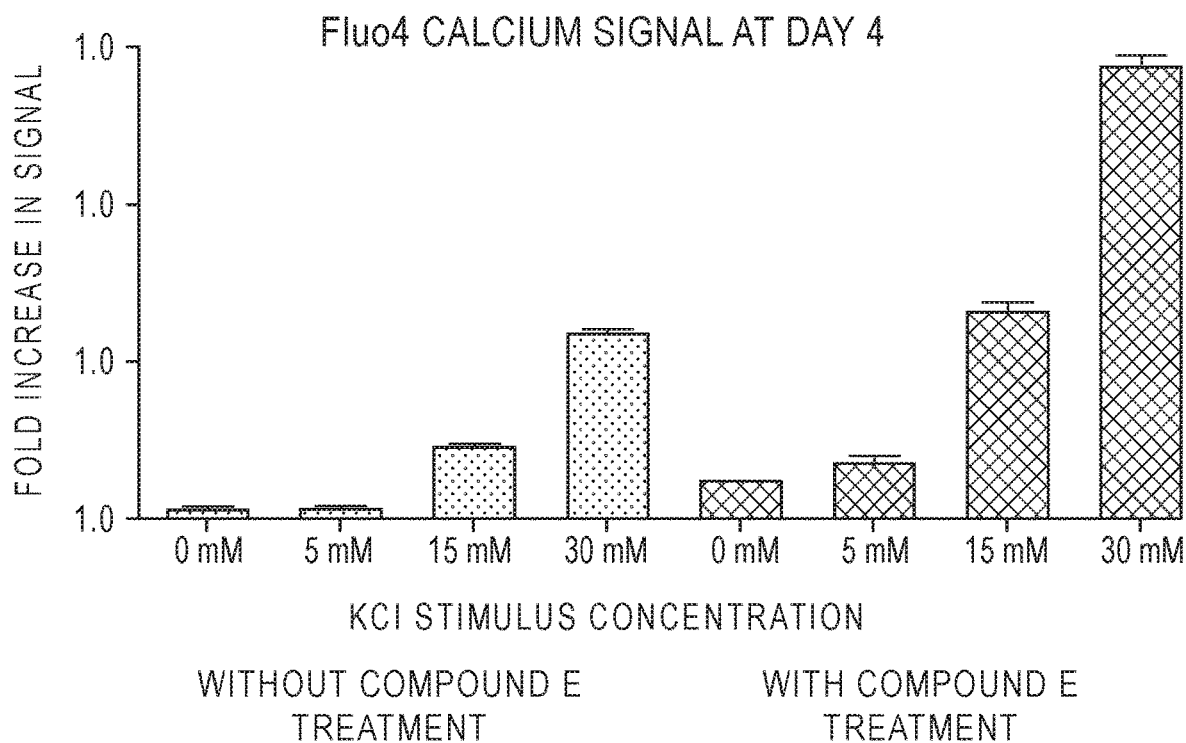
Figure 10B:
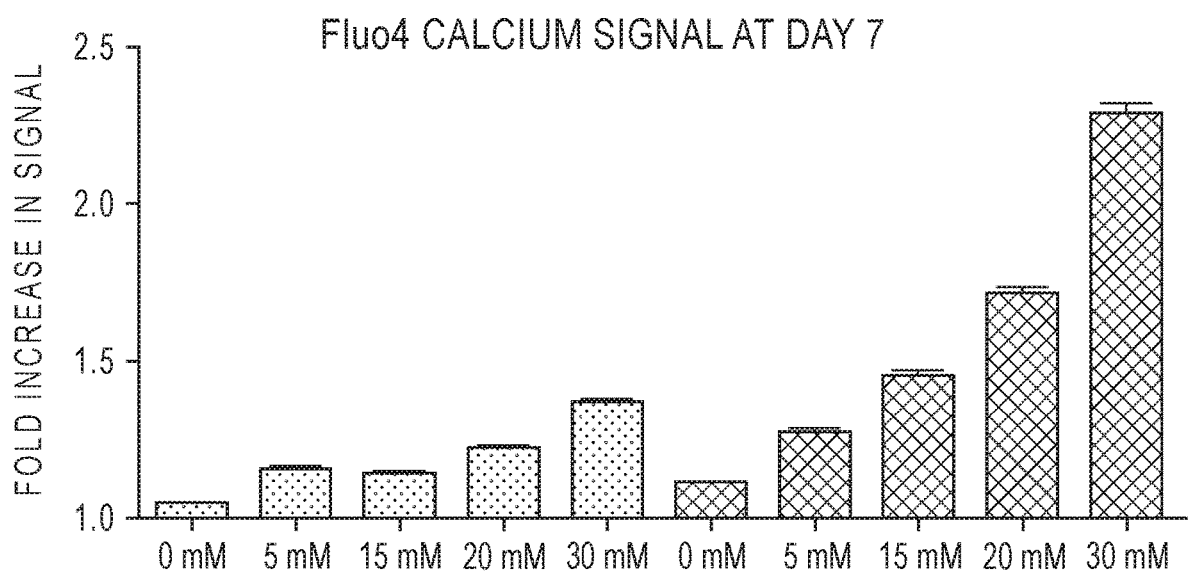

FIG. 10A and FIG. 10B provide tabular data showing the averaged peak calcium responses (n=4-8 each) to NSCs cultured without (dotted bars) and to cultures differentiated in the presence of Compound E to neuronal cells (lined bars) across a range of potassium stimulus strengths at Day 4 (FIG. 10A) and at Day 7 (FIG. 10B).

DESCRIPTION OF VARIOUS EMBODIMENTS

It is to be understood that both the foregoing general description and the following detailed description are exemplary and explanatory only and are not intended to limit the scope of the current teachings. In this application, the use of the singular includes the plural unless specifically stated otherwise. The use of "comprise", "contain", and "include", or modifications of those root words, for example but not limited to, "comprises", "contained", and "including", are not intended to be limiting. Use of "or" means "and/or" unless stated otherwise. The term "and/or" means that the terms before and after can be taken together or separately. For illustration purposes, but not as a limitation, "X and/or Y" can mean "X" or "Y" or "X and Y." As used herein and unless otherwise indicated, the terms "a" and "an" are taken to mean "one," "at least one" or "one or more."

Whenever a range of values is provided herein, the range is meant to include the starting value and the ending value and a value or value range there between unless otherwise specifically stated. For example, "from 0.2 to 0.5" means 0.2, 0.3, 0.4, 0.5; ranges there between such as 0.2-0.3, 0.3-0.4, 0.2-0.4; increments there between such as 0.25, 0.35, 0.225, 0.335, 0.49; increment ranges there between such as 0.26-0.39; and the like.

The section headings used herein are for organizational purposes only and are not to be construed as limiting the subject matter described in any way. All literature and similar materials cited in this application including, but not limited to, patents, patent applications, articles, books, treatises, and internet web pages, regardless of the format of such literature and similar materials, are expressly incorporated by reference in their entirety for any purpose. In the event that one or more of the incorporated literature and similar materials defines or uses a term in such a way that it contradicts that term's definition in this application, this application controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Certain embodiments herein relate to improving the process of differentiation of neural stem cells to differentiated cells having desired cell markers. The methods presented herein improve the yield of differentiated cells, improve the ratio of differentiated cells to undifferentiated cells, improve the purity of the differentiated cell population, and reduce clumping of cells, thereby facilitating quantitation and imaging of the differentiated cells. The methods are particularly applicable to differentiation of neural stem cells to neuronal cells.

Further embodiments herein relate to methods for removal of contaminating cell types in primary cell cultures, e.g., removal of astrocytes from primary neuronal cell cultures.

In embodiments herein, the term, "neural stem cells" means SOX 1 positive neural stem cells (NSCs). NSCs can be obtained in a number of ways, e.g., from human iPSCs using the GIBCO™-PSC Neural Induction Medium as provided by the manufacturer (Cat. No. A1647801, Thermo Fisher Scientific, Waltham Mass.), or using the STEMDIFF™ Neural Induction Medium as provided by the manufacturer (Cat. no. 05835, StemCell Technologies, Cambridge, Mass.), for example. The neural stem cells of embodiments herein are characterized by using cell-type specific antibody markers commonly used for immunocytochemical (ICC) analysis such as those from Thermo Fisher Scientific, for example, use of Antibody Cat. No. PA5-23351 or PA5-23370 having binding specificity and affinity for antigen SOX1, use of Antibody Cat. No. MA1-014, MA1-014D488, MA1-014D550, MA1-014D650, MA1-014HRP, or PA1-094 having binding specificity and affinity for antigen SOX2, or use of Antibody Cat. No. MA1-110 having binding specificity and affinity for antigen NESTIN, for example.

Embodiments of the method provided herein provide for differentiation of SOX positive NSCs to neuronal cells. As used herein, the term "neuronal cells" means cells characterized by using cell-type specific antibody markers used for ICC analysis such as those from Thermo Fisher Scientific, for example, use of Antibody Cat. No. MA5-12823, 13-1500, or MA5-12826 having binding specificity and affinity for antigen MAP2, Antibody Cat. No. A21271 or A21272 having binding specificity and affinity for antigen HuC/D or Antibody Cat. No. 48-1200 having binding specificity and affinity for antigen DCX, for example. In some embodiments herein, the neuronal cell is positive for MAP2 and/or DCX markers.

The phrase "retarding neural stem cell proliferation", as used herein, means arresting, slowing, hindering, or impeding the increase in number of neural stem cells without causing significant cell death. Cell proliferation can be measured by incorporation of the nucleoside thymidine analog EdU which is incorporated into DNA during active DNA synthesis with the result that proliferating cells become labeled. Such measurements are compared from cells cultured with and without presence of the gamma secretase inhibitor as shown in Example 3 herein. The retardation of neural stem cell proliferation, in some embodiments, is at least 10% to at least 20% reduction, at least 20% to at least 40% reduction, at least 20% to at least 40% reduction, or in some embodiments, at least 40% to at least 60% reduction of neural stem cell number in the presence of a gamma secretase inhibitor as compared to the absence of a gamma secretase inhibitor at six days of differentiation. The term "concomitantly," as used herein, means that the retardation of proliferation of some neural stem cells occurs in the same culture in which some cells are differentiating to neuronal cells.

In some embodiments as shown by Example 7, the retardation is at least a 2-fold reduction of neural stem cell number when differentiation occurs in the presence of a gamma secretase inhibitor as compared to when differentiation occurs in the absence of a gamma secretase inhibitor at four days of differentiation. In some embodiments, the retardation is at least a 5-fold reduction of neural stem cell number when differentiation occurs in the presence of a gamma secretase inhibitor as compared to differentiation in the absence of a gamma secretase inhibitor at seven days of differentiation.

Cell death can be measured by staining cells with antibodies against the apoptotic cell death marker caspase 9 as shown by Example 3 herein. The term "without causing significant" cell death means that differentiation in the presence of the gamma secretase inhibitor in an NSC cell culture does not cause an increase in cell death of more than 2- to 4-fold, of more than 4- to 6-fold, of more than 6- to 8-fold or more than 8- to 10-fold as compared to differentiation of the NSC culture in the absence of gamma secretase inhibitor.

The term "accelerating differentiation" of a neural stem cell, as used herein, means that a greater calcium signal is obtained in response to a stimulus when differentiation of neural stem cells to neuronal cells is carried out in the presence of the gamma secretase inhibitor as compared to when differentiation occurs in the absence of the gamma secretase inhibitor as measured, for example, by using components of the Fluo-4 Calcium Imaging Kit (Cat. No. F10489, Molecular Probes, Eugene Oreg.). Calcium signals elicited by potassium depolarization are measured and the measure provides an estimate of the relative number of voltage gated calcium ion channels present on cells in the culture, which is a "proxy" for neuronal signaling and developmental maturity. Mature, excitable cells express large numbers of voltage gated channels that can be opened by depolarizing the cellular membrane with extracellular potassium addition, while immature or non-excitable cells express few or no voltage gated calcium ion channels available for opening with a potassium depolarization stimulus.

This greater calcium signal is observed at least as early as Day 4 of differentiation. Example 7 herein provides data showing that the control culture provided an increase in calcium signal of 23%, 37%, 72% and 112.4% for Day 4, 7, 14, and 21, respectively, while the test culture differentiated in the presence of Compound E provided an increase in calcium signal of 57%, 128%, 116.9% and 286.6% for Day 4, 7, 14, and 21, respectively. These data demonstrate that cells differentiated in the presence of Compound E have greater excitability in response to a stimulus as compared to cells in the same medium without Compound E, indicating that the maturity of the neuronal cells is accelerated.

An accelerated differentiation signal is seen by comparing the signal at Day 4 of 23% in control cultures with the signal of 57% at Day 4 in test cultures, i.e., a culture having a gamma secretase inhibitor present during differentiation. Similarly, an accelerated differentiation signal is seen by comparing the signal at Day 7 of 37% in control cultures with the signal of 128% at Day 7 in test cultures, i.e., a culture having a gamma secretase inhibitor present during differentiation. An accelerated differentiation signal is also seen by comparing the signal at Day 14 of 72% in control cultures with the signal of 116.9% at Day 14 in test cultures, i.e., a culture having a gamma secretase inhibitor present during differentiation. An accelerated differentiation signal is also seen by comparing the signal at Day 21 of 112.4% in control cultures with the signal of 286.6% at Day 21 in test cultures, i.e., a culture having a gamma secretase inhibitor present during differentiation.

In one aspect, the differentiation medium of embodiments herein comprises at least one serum-free neural stem cell culture medium, and a serum-free supplement comprising at least one gamma secretase inhibitor. The differentiation medium, in some embodiments, lacks presence of at least one of leukemia inhibitor) factor (LIF), an inhibitor of glycogen synthase kinase 3 (GSK3), and an inhibitor of transforming growth factor bets (TGF-beta). In some embodiments, the differentiation medium lacks presence of fibroblast growth factor/epidermal growth factor (FGF2/EGF). Every 2-3 days, half spent medium was removed from each well of the culture plates and the same volume of fresh medium was added into each well.

An exemplary serum-free neural stem cell culture medium comprises, for example, NEUROBASAL™ Medium (Brewer et al., *J. Neuroscience Res.,* 35:567-576, 1993; Cat. No. 21103, Thermo Fisher Scientific, Waltham Mass.), 2% B27 Supplement (Cat No. 17504, Thermo Fisher Scientific, Waltham Mass.), 1% GLUTAMAX™ Supplement (Cat. No. 35050, Thermo Fisher Scientific, Waltham Mass.) and 200 micromolar ascorbic acid (Cat. No. A8960, Sigma-Aldrich, St. Louis Mo.).

A further exemplary serum-free neural stem cell culture media comprises DMEM/F12, 1×N2, 1×B27 Supplement (Cat No. 17504, Thermo Fisher Scientific. Waltham Mass.), 300 ng/mL cAMP (Sigma-Aldrich) and 0.2 mM Vitamin C (Sigma-Aldrich) (Li et al. PNAS 108:20, 8299-8304).

Another exemplary serum-free neural stem cell culture media is the STEMPRO™ NSC SFM (Cat. No. A1050901, GIBCO, Grand Island, N.Y.) that contains STEMPRO™ Neural Supplement.

The serum-free supplement of the differentiation medium comprises at least one gamma secretase inhibitor. Known gamma secretase inhibitors (GSIs) include, e.g., GSI I, Z-Leu-Leu-Norleucine-CHO; GSI II; GSI III, N-benzyloxycarbonyl-Leu-leucinal; GSI IV, N-(2-naphthoyl)-Val-phenylalaninal; GSI V, N-benzyloxycarbonyl-Leu-phenylalaninal; GSI VI, 1-(S)-endo-N-(1,3,3)-trimethylbicyclo[2.2.1]hept-2-yl)-4-fluorophenyl sulfonamide; GSI VII, menthyloxycarbotyl-LL-CHO; GSI IX, N—[N-(3,5-difluorophenacetyl-L-alanyl)]-S-phenylglycine t-butyl ester (DAPT); GSI X, {1S-Benzyl-4R-[1-(1S-carbamoyl-2-phenethylcarbamoyl)-1S-3-methylbutylcarb-amoyl]-2R-hydroxy-5-phenylpentyl}carbamic acid tert-butyl ester, GSI XI, 7-amino-4-chloro-3-methoxyisocoumarin; GSI XII, Z-Ile-Leu-CHO; GSI XIII, Z-Tyr-Ile-Leu-CHO; GSI XIV, Z-Cys(t-Bu)-Ile-Leu-CHO; GSI XVI, N—[N-3,5-difluorophenacetyl]-L-alanyl-S-phenylglycine methyl ester; GSI XVII; GSI XIX, (2S,3R)-3-(3,4-Difluorophenyl)-2-(4-fluorophenyl)-4-hydroxy-N-((3S)-2-oxo-5-phenyl-2,3-dihydro-1H-benzole[e][1,4]diazepin-3-yl)-butyramide; GSI XX, (S,S)-2-[2-(3,5-difluorophenyl)-acetylamino]-N-(1-methyl-2-oxo-5-phenyl-2,-3-dihydro-1H-benzo[e][1,4]diazepin-3-yl)-propionamide (Dibenzazepine (DBZ) (YO-01027, SelleckChem); and the hydroxylated form: N-2((2S)-2-(3,5-difluorophenyl)-2-hydroxyethanoyl)-N1-((7S)-5-methyl-6-oxo-6,7-dihydro-5H-dibenzo[b,d]azepin-7-yl)-1-alaninamide (LY411575, Sigma-Aldrich. STEMGENT™); GSI XXI, (S,S)-2-[2-(3.5-difluorophenyl)-acetylamino]-N-(1-methyl-2-oxo-5-phenyl-2,-3-dihydro-1H-benzo[e][1,4] diazepin-3-yl)-propionamide (Compound E, EMD Millipore, Enzo Life Sciences); gamma40 secretase inhibitor I, gamma40 secretase inhibitor II and RO4929097.

In one aspect, the gamma secretase inhibitor is YO-01027. In another aspect, the gamma secretase inhibitor is Compound E. In one aspect, the gamma secretase inhibitor is LY411575. In an aspect, the gamma secretase inhibitor is MK-0752. In another aspect, the gamma secretase inhibitor is LY450139 (Semagacestat). In another aspect, the gamma secretase inhibitor is RO4929097. Gamma secretase inhibitors are commercially available from, e.g., EMD Millipore (Billerica Mass.), APExBIO (Houston Tex.), or from SelleckChem, for example.

In some embodiments, the gamma secretase inhibitor is other than that of group IX (GSI IX), i.e., other than that of DAPT, N—[N-(3,5-difluorophenacetyl-L-alanyl)]-S-phenylglycine t-butyl ester.

In some embodiments, the amount of gamma secretase inhibitor in the supplement is such that dilution thereof into the serum-free neural cell culture medium to generate the differentiation medium provides an amount of inhibitor effective to accelerate differentiation of a neural stem cell to a neuronal cell while retarding neural stem cell proliferation. In some embodiments, the gamma secretase inhibitor is present in the differentiation medium at a concentration of 0.1 micromolar to 80 micromolar, 0.1 micromolar to 40 micromolar, a concentration of 0.1 micromolar to 20 micromolar, a concentration of 0.2 micromolar to 10 micromolar, a concentration of 0.2 micromolar to 2.0 micromolar, a concentration of 0.2 to 1.0 micromolar, or a concentration of 0.2 to 0.5 micromolar. In some embodiments, the final concentration of the inhibitor in the differentiation medium is 0.2 micromolar to less than 0.5 micromolar.

In certain embodiments, when the gamma secretase inhibitor is YO-01027, Compound E, or LY411575, the concentration of the inhibitor in the differentiation medium is 0.01 micromolar to 20 micromolar, 0.1 micromolar to 20 micromolar, 0.2 micromolar to 10 micromolar, 0.2 micromolar to 5 micromolar, 0.2 micromolar to 2.0 micromolar, 0.2 to 1.0 micromolar, or a concentration of 0.2 to 0.5 micromolar. In some embodiments, the final concentration of the inhibitor in the differentiation medium is 0.2 micromolar to less than 0.5 micromolar.

In another aspect, when the gamma secretase inhibitor is RO4929097, LY450139 (Semagacestat) or MK-0752, the concentration in the differentiation medium is 0.8 micromolar to 80 micromolar, 1.0 micromolar to 60 micromolar, 5 micromolar to 60 micromolar, 10 micromolar to 50 micromolar, or 20 micromolar to 50 micromolar.

Serum-free supplement ingredients may include in addition to the gamma secretase inhibitor, optionally, one or more of progesterone, sodium selenite, recombinant human insulin, putrescine, and human transferrin holoenzyme. In some embodiments, the serum-free supplement may include, in addition to the gamma secretase inhibitor, the N-2 supplement (Thermo Fisher Scientific. Waltham Mass.).

Cells are plated generally on a matrix such as laminin, collagen IV, fibronectin, vitronectin, polylysine, polyomitine, or a combination thereof such as, for example, basement membrane matrices available such as GELTREX™ (Thermo Fisher Scientific, Waltham Mass.) or MATRIGEL™ (Fisher Scientific, Waltham Mass.). In one embodiment, the matrix includes laminin.

As used herein, the term "salt thereof" with reference to a gamma secretase inhibitor refers to an acid or base addition salt that retains the biological efficacy and properties of the inhibitor and is made using acids or bases as appropriate. Exemplary acid addition salts include, e.g., HCl, HBr, HI, $H_2SO_4$, nitric acid, phosphoric acid and sulfamic acid, as well as those made using acids such as citric acid, fumaric acid, lactic acid, malic acid, methanesulfonic acid, oxalic acid, salicylic acid, succinic acid, p-toluenesulfonic acid, and the like. Exemplary base addition salts include, e.g., those made using hydroxides of ammonia, potassium, or sodium, such as tetramethylammonium hydroxide.

In a method of treating a subject having a neurodegenerative condition, the administration of a pharmaceutical composition containing neuronal cells made by methods as described herein may be by implantation, injection, or transplantation, for example. In one aspect, the neuronal cells are differentiated from neural stem cells autologous for the subject, that is, the neural stem cells are autologous by way of induction of stem cells obtained from the subject to neural stem cells. The differentiation is ex vivo prior to administration. In another aspect, the neuronal cells are derived from a neural stem cell induced from stem cells allogeneic for the subject and differentiation is ex vivo prior to administration. The neurodegenerative condition may be, e.g., Parkinson's disease, Huntington's disease, stroke effects, or dementia such as Alzheimer's conditions, and administration may be, e.g., to the central nervous system.

A "pharmaceutical composition" of a gamma secretase inhibitor is substantially non-toxic to the subject to which the composition is administered. A "therapeutically effective amount" is an amount of gamma secretase inhibitor, or the amount of a composition or pharmaceutical composition containing the gamma secretase inhibitor that is effective for producing a desired therapeutic effect upon administration to a patient.

Embodiments herein are further illustrated by the following examples, which are not to be construed as imposing limitations upon the scope of the appended claims.

Example 1—Retarding Proliferation Concomitantly with Differentiating iPSC-Derived Neural Stem Cells to Neuronal Cells Human induced pluripotent stem cells were derived from human fibroblasts using the CYTOTUNE™-iPS 2.0 Sendai Reprogramming Kit (Cat No. A16517, INVITROGEN™, a part of Thermo Fisher Scientific, Waltham Mass.) and were induced to neural stem cells (NSCs) using the xeno free version of the GIBCO™ PSC Neural Induction Medium (Cat. No. A1647801. Thermo Fisher Scientific, Waltham Mass.).

To differentiate the NSCs into neuronal cells, cryo-preserved iPSC-derived NSCs were recovered and NSC passage three cells were plated on a 24 well plate (Cat. No. 087721, Thermo Fisher Scientific, Waltham Mass.) coated with human laminin (Cat. No. L6274, Sigma-Aldrich, St. Louis Mo.) at a density of $1-5\times10^4$ cells/cm². The cultures were maintained in neuronal differentiation medium containing NEUROBASAL™ Medium (Cat. No. 21103, Thermo Fisher Scientific, Waltham Mass.), 2% B27 Xeno Free Supplement (Cat. No. A1486701, Thermo Fisher Scientific, Waltham Mass.), 200 micromolar ascorbic acid (Cat. No. A8960, Sigma-Aldrich, St. Louis Mo.) with or without the gamma-secretase inhibitor Compound E (0.1 micromolar, Cat. No. 565790, EMD Millipore, Billerica Mass.). Every 2-3 days, medium was replenished with respective medium.

Phase images were monitored and differentiated cells were fixed at Day 7 and Day 15 with 4% paraformaldehyde and stained with antibodies against the neuronal marker DCX (polyclonal, Cat. No. 48-1200, Thermo Fisher Scientific, Waltham Mass.) and the neural stem cell marker NESTIN (Monoclonal, Cat. No. 611658, BD Biosciences, Franklin Lakes N.J.) according to the manufacturers' protocols.

Figure 1A:
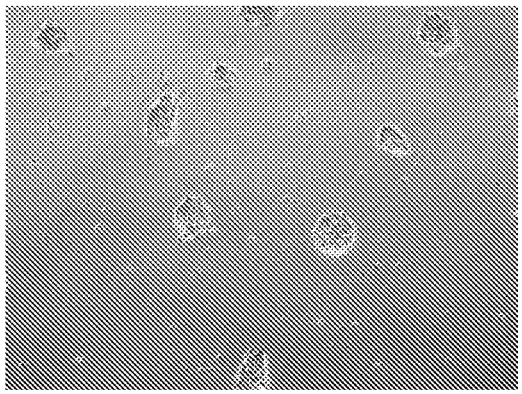
Figure 1B:
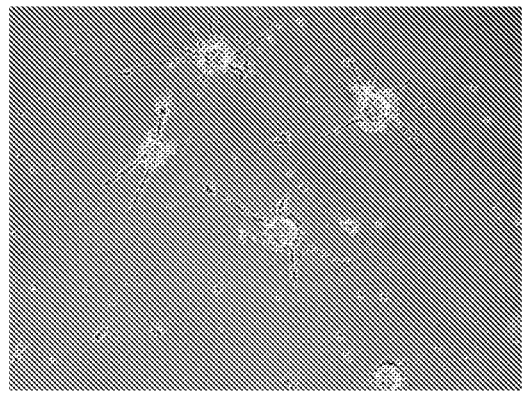

Differences between cultures with and without Compound E were observed as early as 5 days of differentiation as shown by comparing the image of FIG. 1A of cells without Compound E with the image of FIG. 1B of cells differentiated in the presence of Compound E. Cells without Compound E lack marked neurite outgrowth whereas cells with Compound E developed neuronal cells with extended neurite outgrowth.

Figure 1C:
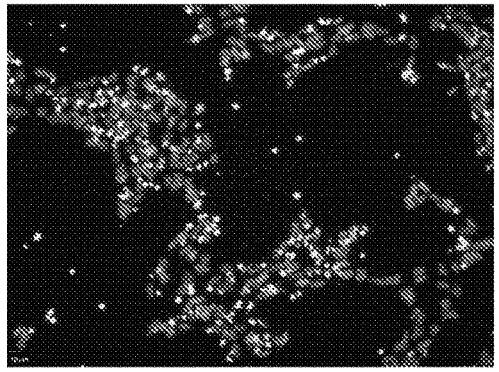
Figure 1D:
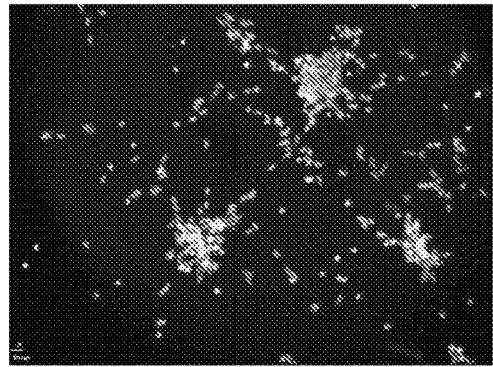
Figure 1E:
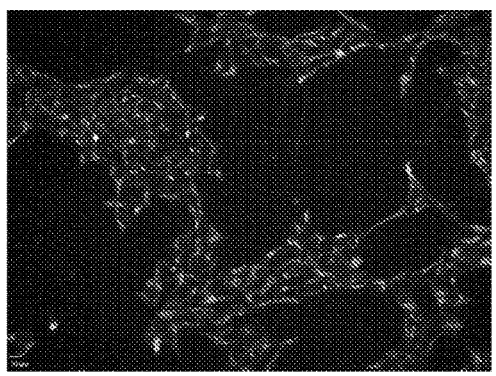
Figure 1F:
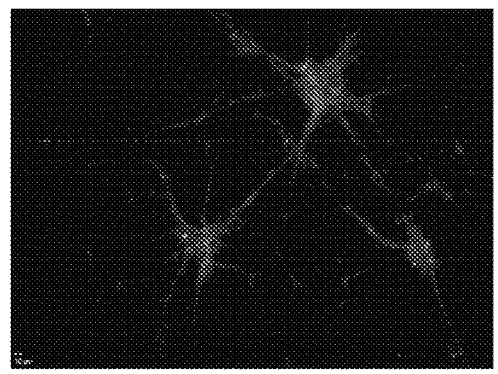
Figure 1G:
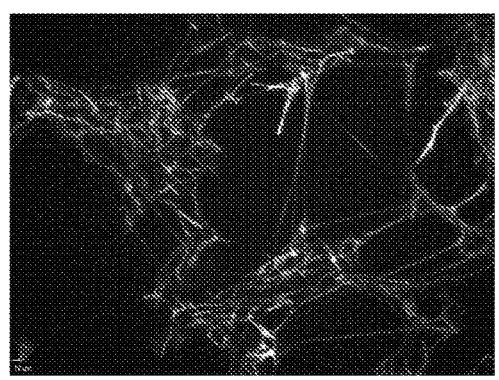
Figure 1H:
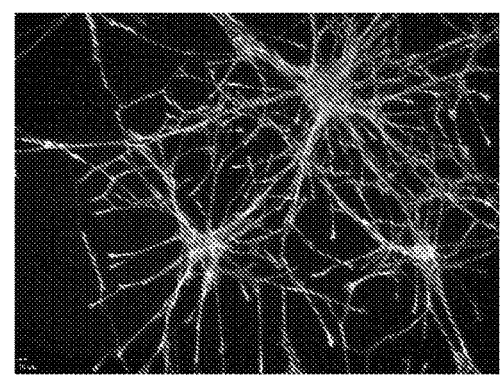

FIG. 1C shows cells stained with DAPI, a nuclear stain, thereby showing all cells in the culture at Day 7 of differentiation without Compound E. FIG. 1E shows the same set of cells stained with NESTIN, a marker for neural stem cells, while FIG. 1G shows again the same set of cells stained with DCX, a neuronal marker. Cells differentiated without the presence of Compound E have a mixed phenotype of neural stem cells and neuronal cells. FIG. 1D shows cells stained with DAPI, the nuclear stain, thereby showing all cells in the culture at Day 7 of differentiation in the presence of Compound E. The phenotype was further examined with imaging the same set of cells using the neural stem cell marker NESTIN (FIG. 1F) and the neuronal marker DCX (FIG. 1H) at Day 7 of differentiation. Cells differentiated in the presence of Compound E have had proliferation of NESTIN positive cells substantially retarded while most of the cells present have adopted a neuronal phenotype as shown by the stain for DCX.

Figure 1I:
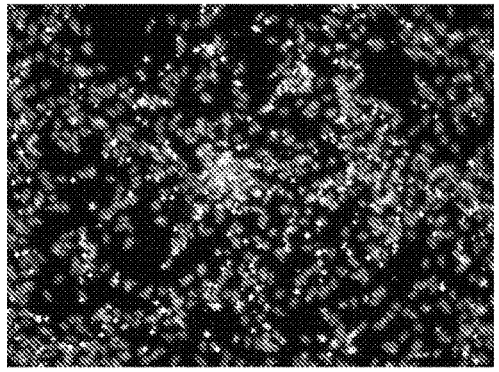
Figure 1J:
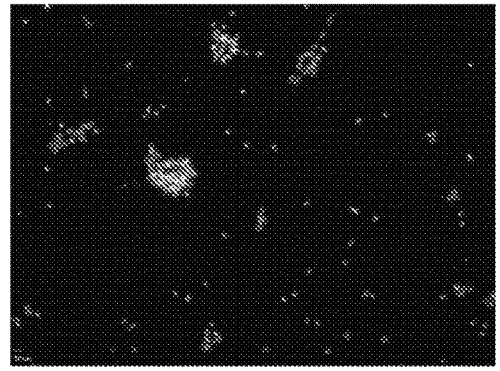
Figure 1K:
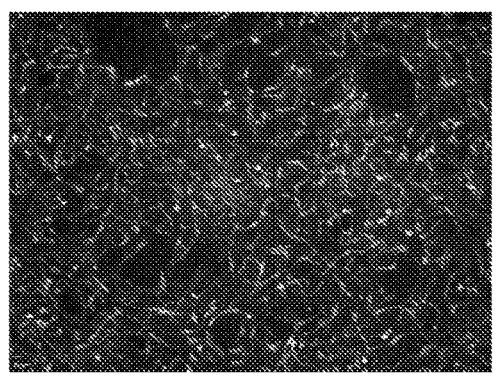
Figure 1L:
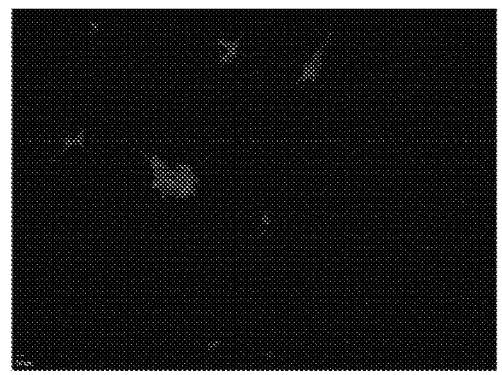
Figure 1M:
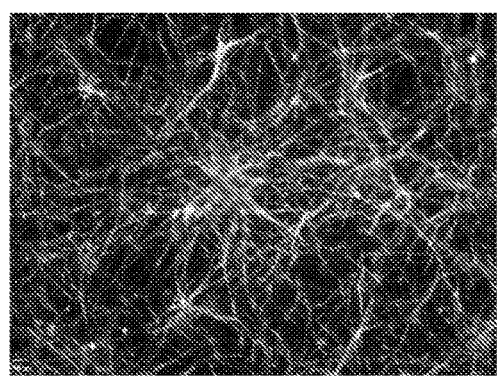
Figure 1N:
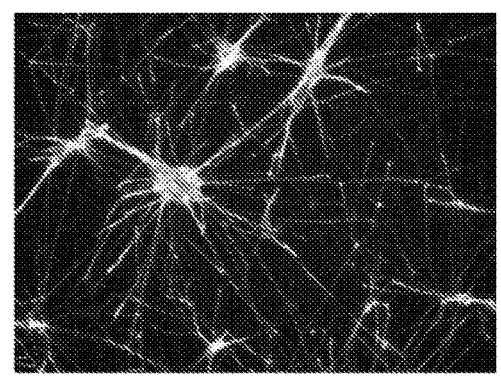

At Day 14, the effect of the presence of Compound E in the differentiation medium is more apparent. Images of FIG. 1I (DAPI is a marker for nuclei), FIG. 1K (NESTIN is a marker for neural stem cells) and FIG. 1M (DCX is a marker for neuronal cells) show that cells are proliferating and differentiating in the absence of Compound E. In contrast, fewer proliferating progenitor cells are present in the images of cultures having Compound E present (FIG. 1J, FIG. 1L and FIG. 1N). However, most of those cells appear to be neuronal cells as indicated by the stain for neuronal marker DCX.

Example 2—Retarding Proliferation Concomitantly with Differentiating hESC-Derived Neural Stem Cells to Neuronal Cells H9 human embryonic stem cell (ESC)-derived neural stem cells (NSCs) were induced and expanded using the GIBCO™-PSC Neural Induction Medium (Cat. No. A1647801. Thermo Fisher Scientific, Waltham Mass.), a serum-free medium in which human PSCs are converted into NSCs in one week with high efficiency and without the laborious processes of embryonic body (EB) formation and mechanical NSC isolation.

To differentiate the NSCs into neuronal cells, cryo-preserved H9 ESC-derived NSCs were thawed and plated on poly-D-lysine 96-well plates (Cat No. 08-774-255, Thermo Fisher Scientific, Waltham Mass.) coated with laminin (Cat. No. 23017, Thermo Fisher Scientific, Waltham Mass.) at a density of $5\times10^4$ cells/cm². The cultures were maintained in the neuronal differentiation medium containing NEUROBASAL™ Medium (Cat. No. 21103, Thermo Fisher Scientific. Waltham Mass.), 2% B27 Supplement (Cat. No. 17504, Thermo Fisher Scientific, Waltham Mass.), 1% GLUTAMAX™ Supplement (Cat. No. 35050, Thermo Fisher Scientific, Waltham Mass.) and 200 micromolar ascorbic acid (Cat. No. A8960, Sigma-Aldrich, St. Louis Mo.) with or without the gamma-secretase inhibitor Compound E (0.2 micromolar. Cat. No. 565790, EMD Millipore, Billerica Mass.). Every 2-3 days, half spent medium was removed from each well of the culture plates and the same volume of fresh medium was added into each well.

At two weeks of NSC differentiation into neuronal cells, cells were fixed with 4% paraformaldehyde and stained with antibodies against neuronal marker MAP2 (polyclonal, Cat. No. PA5-17646, Thermo Fisher Scientific, Waltham Mass.) and neural stem cell marker SOX1 (polyclonal, Cat. No. AF3369, R&D Systems, Minneapolis Minn.) according to the manufacturers' protocols.

Figure 2A:
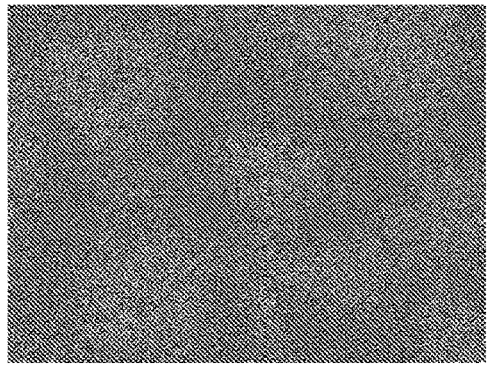

At the end of that two week period, cells without gamma-secretase inhibitor treatment almost reached confluence (FIG. 2A). Although a portion of cells extended neurites and showed the morphology of neuronal cells, the majority of cells formed cell clumps without neurite extension as shown in FIG. 2A. Immunocytochemical staining showed that cells lacking gamma-secretase inhibitor present in the differentiation medium contained a mixed population of MAP2 positive neuronal cells (FIG. 2C) and a substantial number of SOX1 positive NSCs as shown in FIG. 2E. In the culture without gamma-secretase inhibitor treatment, SOX 1 positive NSCs kept dividing which led to a high density of undesired NSCs and clump formation (FIG. 2A).

Figure 2B:
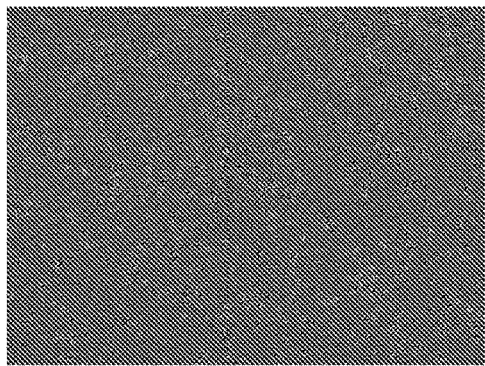
Figure 2C:
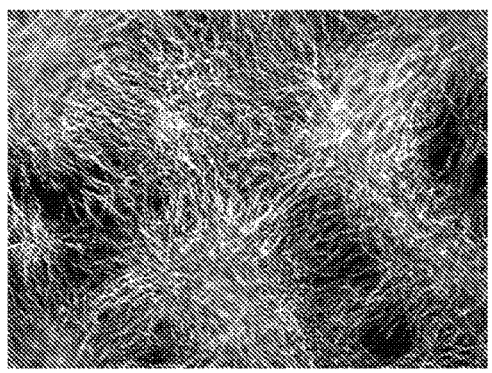
Figure 2D:
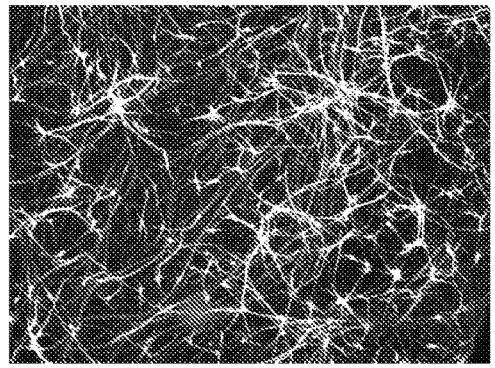
Figure 2E:
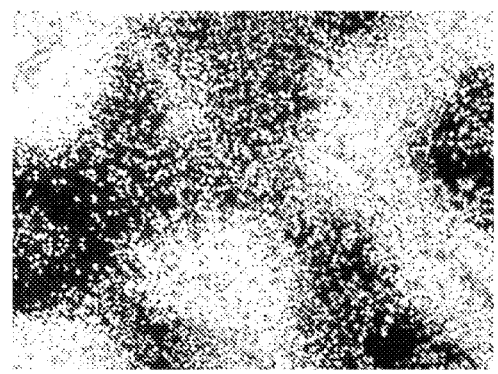
Figure 2F:
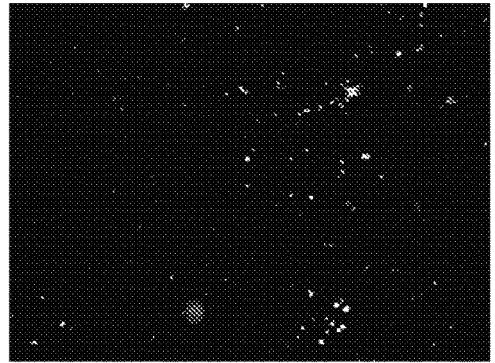

In contrast, cells with gamma-secretase inhibitor present in the differentiation medium were distributed evenly without the formation of cell clumps as shown by FIG. 2B and nearly every cell extended neurites (FIG. 2D). Also, in cells differentiated in the presence of the gamma-secretase inhibitor, nearly all cells were MAP2 positive neuronal cells (FIG. 2D) with only a few SOX1 positive cells (FIG. 2F).

Figure 3:
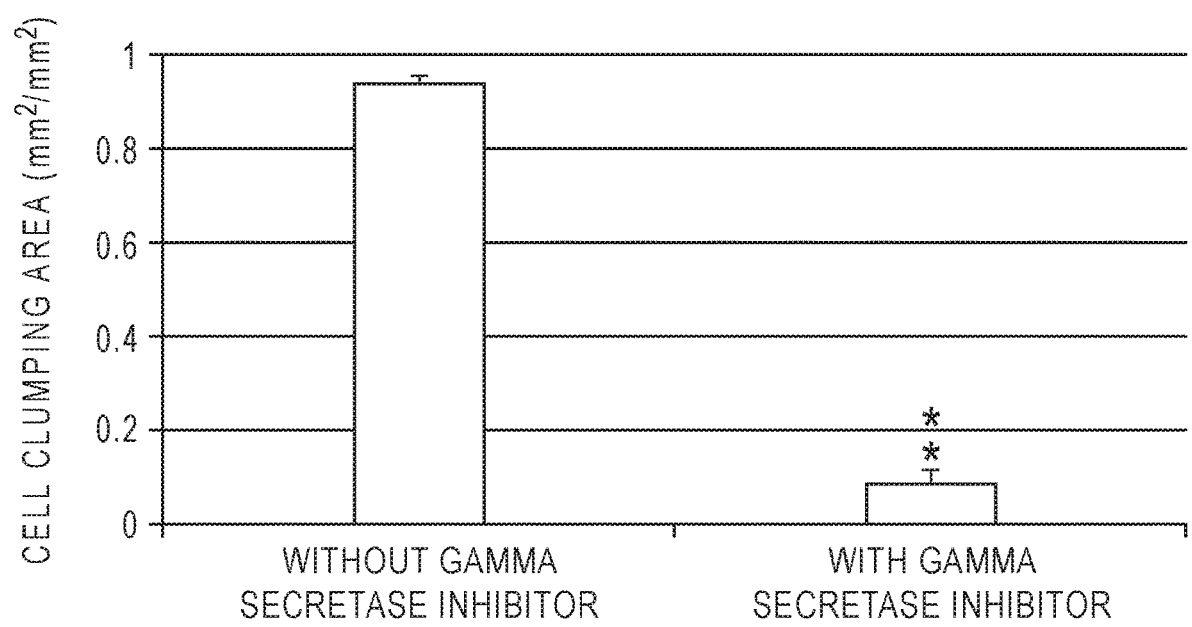

Also, at the end of that two week period of differentiation, the area of cell clumps was calculated using the INCUCYTE ZOOM™ System (Essen BioScience, Ann Arbor Mich.) by defining the area of cell mass $\geq 10,000$ µm² as a cell clump. The data of FIG. 3 show a 90% reduction in cell clumping as a result of the presence of the gamma secretase inhibitor.

Example 3—Retarding Proliferation is not Accompanied by Cell Death

Differentiation of H9 ESC-derived NSCs was the same as for Example 2. At Day 6 of differentiation, cells were incubated with the nucleoside thymidine analog EdU for 24 h. EdU is incorporated into DNA during active DNA synthesis with the result that proliferating cells become labeled. EdU positive cells were detected using the CLICK-IT™ EdU Alexa FLUOR™ 488 HCS Assay (Cat No. C10350, Thermo Fisher Scientific, Waltham Mass.) according to the manufacturer's protocols. Cells were then fixed with 4% paraformaldehyde and stained with antibodies against the apoptotic cell death marker caspase 9 (polyclonal, Cat. No. PA5-16358, Thermo Fisher Scientific, Waltham Mass.) according to the manufacturer's protocol.

Figure 4A:
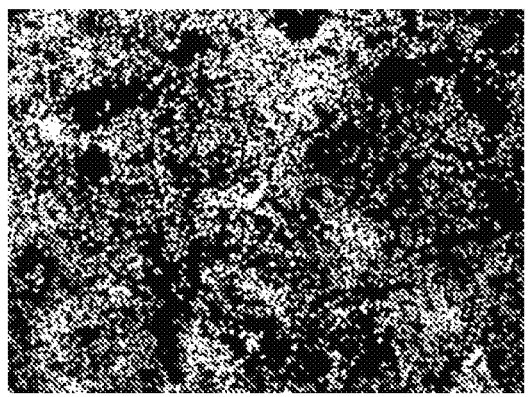
Figure 4B:
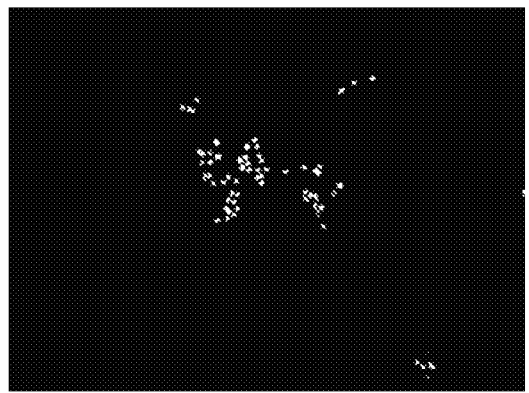
Figure 4C:
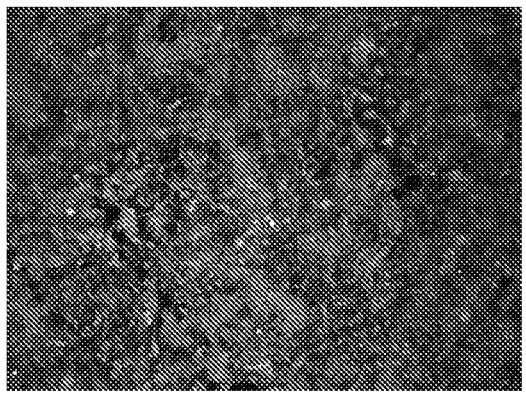
Figure 4D:
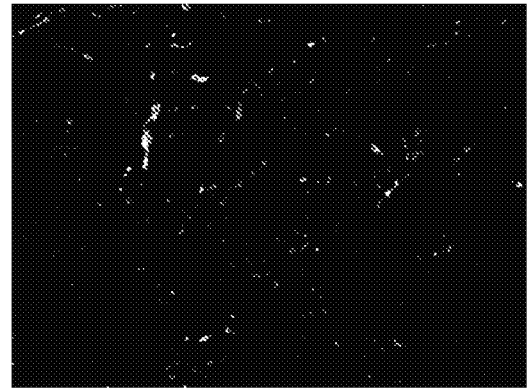

Without gamma-secretase inhibitor presence in the differentiation medium, a substantial portion of EdU positive cells were present in the culture as shown by FIG. 4A. In contrast, only a few EdU positive cells were observed in cultures differentiated in the presence of the gamma-secretase inhibitor (FIG. 4B). In both cultures, where the gamma-secretase inhibitor was absent (FIG. 4C) or where the inhibitor was present during differentiation (FIG. 4D), a very low portion of cells were positive for the cell death marker caspase 9.

Figure 5A:
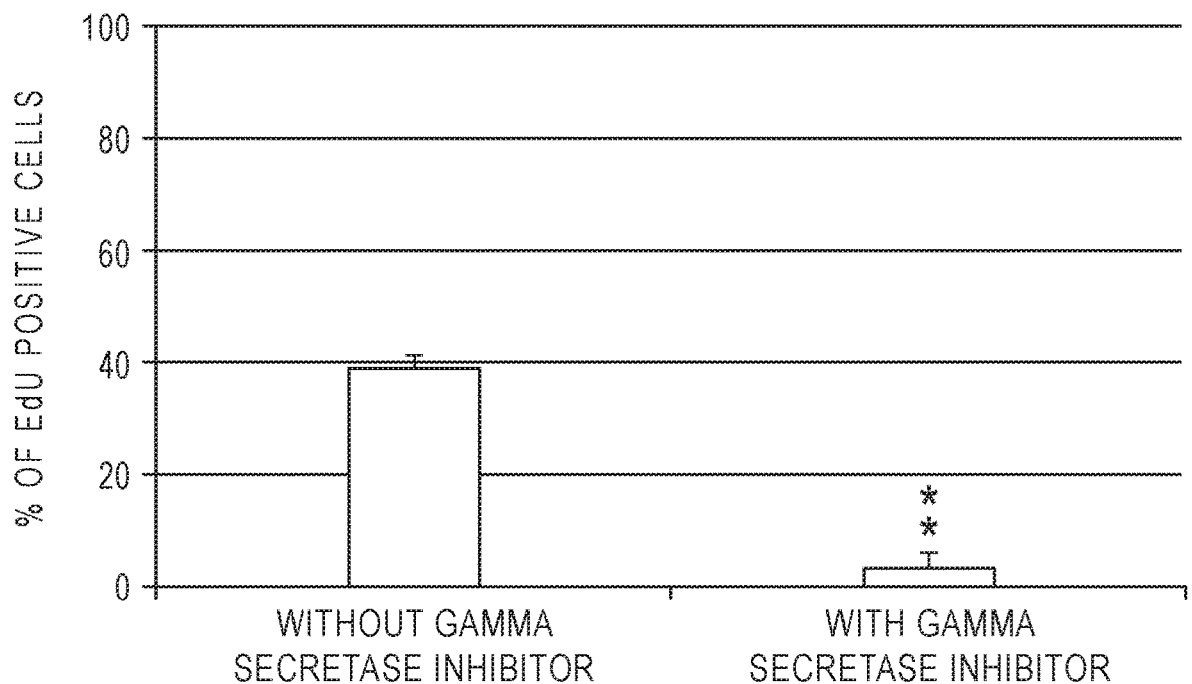
Figure 5B:
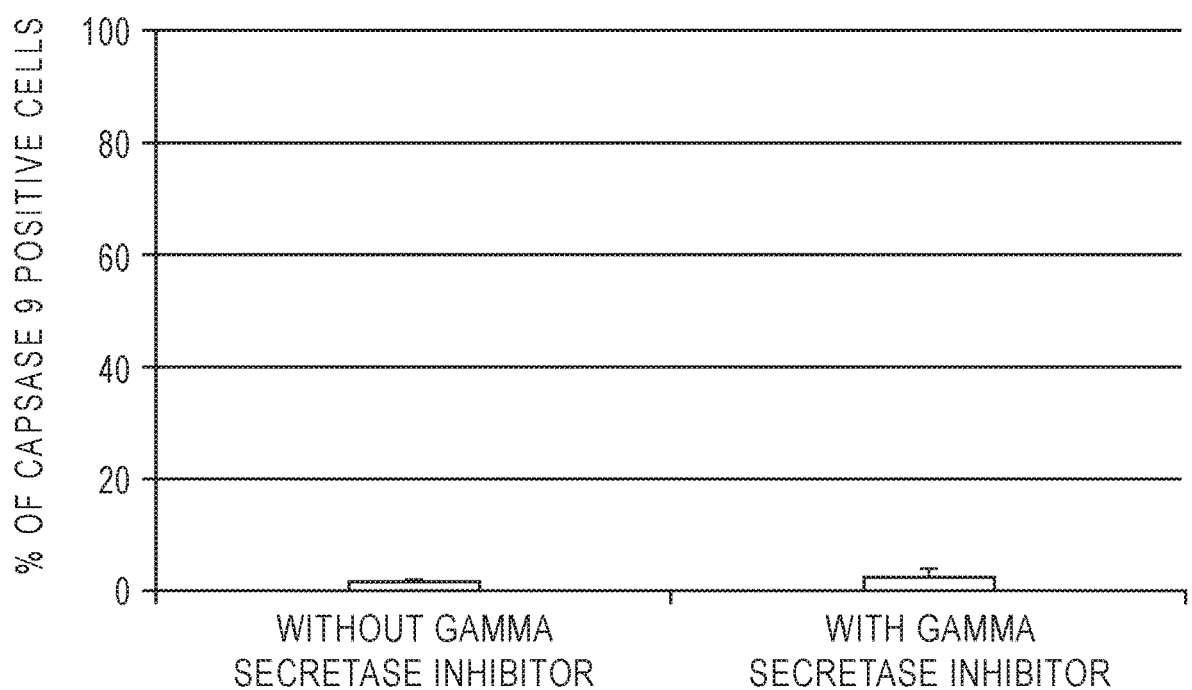

These data are plotted in FIG. 5A and FIG. 5B. FIG. 5A shows a significant reduction in percentage of EdU positive cells as a result of the presence of the gamma-secretase inhibitor in the differentiation medium, that is, a significant reduction in proliferation has occurred. The data of FIG. 5B show a very low percentage of caspase 9 positive cells with or without presence of the gamma-secretase inhibitor during differentiation, that is, very little cell death is occurring in each culture.

Taken together, these results suggest that the effect of cell clump reduction by the gamma-secretase inhibitor is to prevent, arrest or retard cell proliferation without inducing significant cell death.

Example 4—Effect of Various Gamma Secretase Inhibitors on Differentiation of NSCs Examples 1, 2 and 3 focused on the use of Compound E during neural stem cell differentiation to neuronal cells. The present example compares the effect of various other gamma secretase inhibitors and concentrations on that process versus the effect of Compound E.

The differentiation of H9 ESC-derived NSCs was the same as for Example 2. Cells cultured in differentiation medium without the presence of the gamma-secretase inhibitor served as a control. In the test groups, cells were separately differentiated in the presence of Compound E at 0.2 micromolar, YO-01027 at concentrations of 0.3 micromolar, 1.5 micromolar and 7.5 micromolar, LY411575 at concentrations of 0.01 micromolar, 0.05 micromolar, 0.25 micromolar, 0.5 micromolar, 1.0 micromolar and 2.0 micromolar, and MK-0752 at concentrations of 0.8 micromolar, 4 micromolar, 20 micromolar, 40 micromolar and at 80 micromolar. Eight wells were tested for each concentration of each inhibitor.

Figure 6:
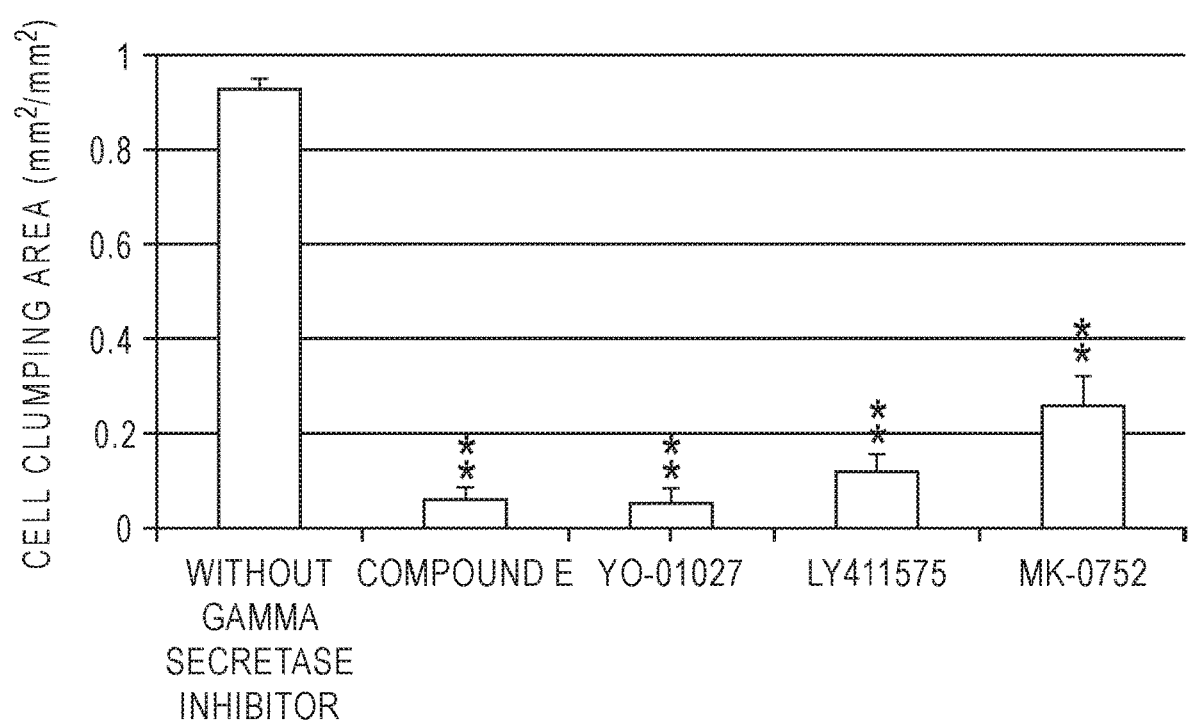

At the end of a two week period of differentiation, the area of cell clumps was calculated for each test well using the INCUCYTE ZOOM™ System (Essen BioScience, Ann Arbor Mich.) by defining the area of cell mass ≥10,000 μm² as a cell clump and the data plotted in FIG. 6. The data of FIG. 6 show results from Compound E at 0.2 micromolar, YO-01027 at 0.3 micromolar, LY411575 at 0.25 micromolar and MK-0752 at 20 micromolar. A significant reduction in cell clumping resulted from the presence of the gamma-secretase inhibitor during differentiation as compared with the cell clump area in the control group. The results showed similar effects on neurite length and cell clumping area of differentiated neuronal cells from hESC-derived NSCs for Compound E at 0.2 micromolar, for YO-01027 at 0.3 micromolar, for LY411575 at 0.5 micromolar, 1 micromolar and at 2 micromolar, and for MK-0752 at a concentration of 40 micromolar and 80 micromolar. Use of MK-0752 at 160 micromolar showed cell toxicity.

Table I provides the percentage of cells that co-stained positive for HuC/D (a neuronal marker) and negative for SOX 1 (a neural stem cell marker) from immunofluorescent image analysis.

TABLE I

| Compound E at 0.2 micromolar | YO-01027 at 0.3 micromolar | LY411575 at 0.25 micromolar | MK-0752 at 20 micromolar |
|---|---|---|---|
| 74.9% | 73.4% | 64.7% | 64.7% |

Note that a 20 micromolar concentration of the inhibitor MK-0752 generated 64.7% of the cells as differentiated cells while 0.2 micromolar Compound E generated 74.9% differentiated cells. These results suggest that, while the effect of cell clump reduction during the differentiation of hPSC-derived NSCs may be a common feature of the gamma-secretase inhibitors tested herein, their efficacy varies. Those compounds having an acetamido backbone appear most effective (in some commercial chemical names, the term "acetylamino" is used to refer to the same backbone structure).

Example 5—Long-Term Maintenance of Differentiated Neuronal Cells

Figure 7A:
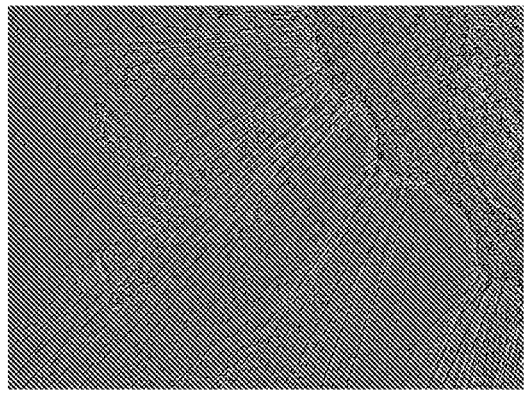
FIG. 7A and FIG. 7B show that differentiated neuronal cells detached from the culture plate at three weeks without the presence of Compound E (FIG. 7A) while neuronal cells differentiated in the presence of Compound E can be maintained to at least five weeks (FIG. 7B).
Figure 7B:
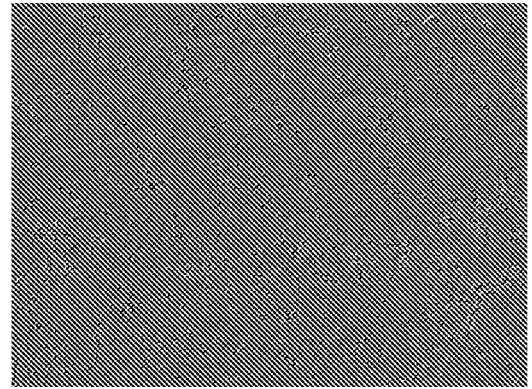

For this study, the differentiation of H9 ESC-derived NSCs was the same as for Example 2. Without presence of the gamma secretase inhibitor during differentiation, neuronal cells detached from the culture plate at three weeks after differentiation as shown by the image of FIG. 7A. This effect may be due to the very high density of proliferated neural stem cells present. Cells cultured in the presence of the gamma secretase inhibitor differentiated into neuronal cells and were maintained at least for five weeks as shown by the image of FIG. 7B with an even distribution of differentiated neuronal cells.

Example 6—Differentiation of Primary Rodent Neuronal Cells

Cryopreserved primary rat cortical neuronal cells (Cat. No. A1084001, Thermo Fisher Scientific, Waltham Mass.), which had been isolated from rodent embryonic brain, were thawed and plated on poly-D-lysine 96-well plates (Cat. No. 08-774-255, Thermo Fisher Scientific, Waltham Mass.) coated with laminin (Cat. No. 23017, Thermo Fisher Scientific, Waltham Mass.) at a density of 8×104 cells/cm2. The culture medium was neuronal differentiation medium containing NEUROBASAL™ Medium (Cat. No. 21103, Thermo Fisher Scientific, Waltham Mass.), 2% B27 Supplement (Cat. No. 17504, Thermo Fisher Scientific, Waltham Mass.), 1% GLUTAMAX™ Supplement (Cat. No. 35050, Thermo Fisher Scientific, Waltham Mass.) without or with gamma secretase inhibitor Compound E. Every 2-3 days, half spent medium was removed from each well of the culture plates and the same volume of fresh medium was added into each well. At two weeks of differentiation, cells were fixed with 4% paraformaldehyde and stained with antibodies against neuronal marker HuC&D and astroglial marker glial fibrillary acidic protein (GFAP).

Figure 8A:
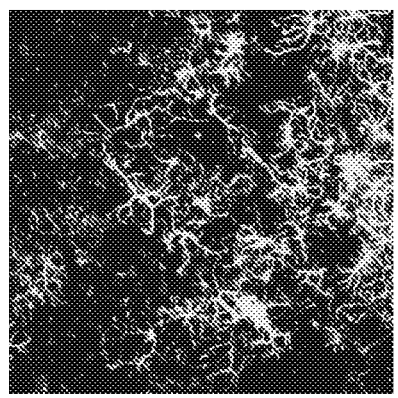
FIG. 8A-FIG. 8D show immunofluorescent images for the astrocyte marker GFAP (FIG. 8A and FIG. 8B) and for the neuronal marker HuC&HuD (FIG. 8C and FIG. 8D) for primary rat cortical neuronal cells differentiated without and with presence of Compound E in the differentiation medium. Presence of Compound E in the differentiation medium substantially eliminated the astrocytes.
Figure 8B:
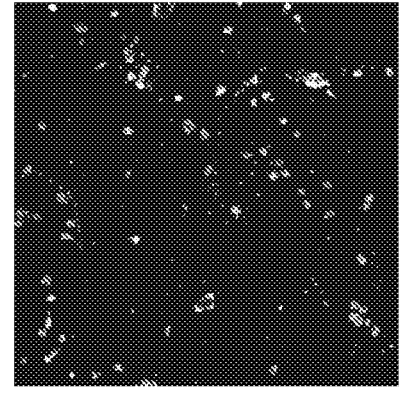
Figure 8C:
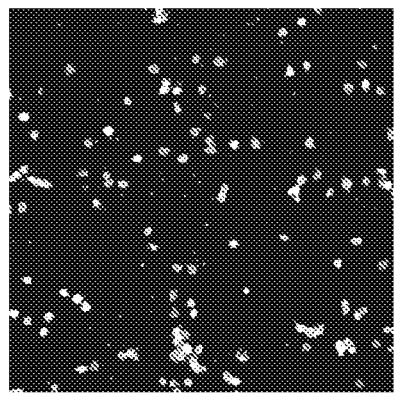
Figure 8D:
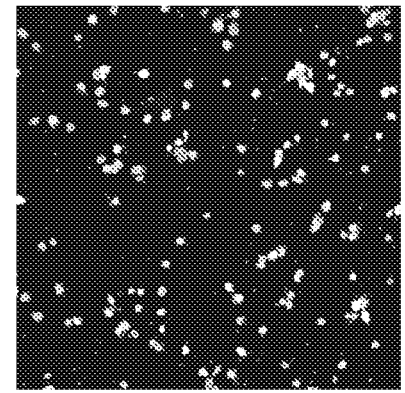

Without gamma secretase inhibitor presence in the differentiation medium, resultant cells contained a large number of GFAP positive astrocytes (FIG. 8A) as well as Hu C & Hu D positive neuronal cells (FIG. 8C). However, cells treated with the gamma secretase inhibitor compound E showed that GFAP positive astrocytes were essentially eliminated (FIG. 8B) with only Hu C & Hu D positive neuronal cells present in the culture (FIG. 8D).

Example 7—Proliferation and Electrophysiology of Differentiated Neuronal Cells as Compared to Neural Stem Cells The proliferation and electrophysiology of cells resulting from differentiation in the presence of Compound E were compared to NSC control cultures. NSC cultures were plated at 20,000 cells per well on Day 0.

The CYQUANT™ Direct Cell Proliferation Assay (Molecular Probes Cat. No. C35011, Eugene Oreg.) was used to provide quantitation of proliferation at Day 4 and Day 7 of culture. As shown by FIG. 9A, at Day 4, the relative fluorescence units (RFU) measurement for the control culture (n=8) had a value of 0.93 and the RFU measurement for cultures differentiated in the presence of Compound E (n=7) had an RFU value of 0.36, an approximate 2.5-fold reduction in cell count. A visual inspection of the cells showed robust proliferation in the control culture with virtually no neurite growth while the cultures differentiated in the presence of Compound E had fewer cells and those cells had elaborated long processes (images not shown).

Compared to the data at Day 4, FIG. 9B shows the same assay measurement at Day 7 for control cultures (n=8) having an RFU of 2.94 (more than a 3-fold increase in number than at Day 4) and for cultures differentiated in the presence of Compound E (n=8) having an RFU of 0.55 (about a 1.5-fold increase). These results indicate that the NSC control cultures continue to proliferate while the cells cultured in the presence of Compound E do not proliferate at the rate of the NSCs without Compound E. These data are consistent with that of Example 3 in that the cells differentiated in the presence of Compound E are terminally differentiated neuronal cells and are not in active DNA synthesis.

At Day 14, the same assay measurement for control cultures (n=8) had an RFU of 18.7 (~a 20-fold increase in number than at Day 4) and cultures differentiated in the presence of Compound E (n=8) had an RFU of 0.41 (a drop as compared to Day 7).

At Day 21, the same assay measurement for control cultures (n=8) had an RFU of 21.5 and cultures differentiated in the presence of Compound E (n=8) had an RFU of 0.30.

The electrophysiology of the NSC control culture and the culture differentiated in the presence of Compound E was studied using dye and quencher components from the Fluo-4 Calcium Imaging Kit (Molecular Probes Cat. No. F10489, Eugene Oreg.) which provides for detection of calcium flux by fluorescence imaging. Mature neurons express voltage gated calcium ion channels that open in proportion to the concentration of a stimulus. For example, with this kit, graded potassium additions to the medium induce a graded depolarization on the membrane. More excitable cultures have larger responses in proportion to neuronal maturity.

Control and test cultures were depolarized with 0, 5, 15, and 30 mM added KCl from an isotonic stimulus. Representative traces of fluorescent response to the addition of the 30 mM KCl stimulus to control NSC cultures and to cultures differentiated in the presence of Compound E to neuronal cells are provided by FIG. 9C which is a plot of signal vs time for measuring calcium flux (average of 8 wells). The signal is measured at 1 hZ and plotted in a running average of multiple wells as fold increase, designated as (signal max−signal min)/signal min. Peak responses were averaged+/−two seconds for each well.

The data are shown in FIG. 9C for Day 4 of differentiation; the basal signal is unchanged in all wells at or near a value of 1, until the potassium chloride stimulus is injected into the solution above the cells. The depolarizing influence to the cellular membrane elicited an increase in cytosolic calcium in proportion to the expression of voltage gated calcium ion channels opened on the cells. Without Compound E in the differentiation medium, the NSCs provided an about 23% increase in response over baseline. With Compound E in the differentiation medium, the differentiated cells provided an about 57% increase in response over the baseline. Given that a much larger calcium response is coming from a smaller number of cells, these data are interpreted to mean that the cells express significantly higher copy numbers of calcium ion channels, which are an important marker for neural maturity and excitability.

FIG. 10A provides tabular data of these electrophysiological results at Day 4. An increased cytosolic calcium response to the potassium chloride stimulus can be seen across the entire range of concentrations of KCl when comparing the cultures without compound E treatment with those cultures differentiated in the presence of Compound E, indicating an increased expression of voltage gated calcium ion channels in the differentiated cultures as a result of Compound E presence.

Tabular results from Day 7 are provided in FIG. 10B. Without Compound E in the differentiation medium and in response to the addition of the 30 mM KCl stimulus, the NSCs provided an about 37% increase in response over baseline. With Compound E in the differentiation medium at Day 7, the response to the addition of the 30 mM KCl stimulus was an about 128% increase over the baseline. Again, there is a much greater response from a smaller number of cells in the cultures differentiated in the presence of Compound E as compared to the number of cells cultured in the absence of Compound E. The 7 day differentiated cells (those treated with Compound E) as measured by this assay demonstrate greater neural maturity and excitability in response to a stimulus as compared to those not treated with Compound E.

Data from Day 14 from cultures differentiated without Compound E in the differentiation medium and in response to the addition of the 30 mM KCl stimulus show that the NSCs provided an about 72% increase in calcium response over baseline. With Compound E in the differentiation medium at Day 14, the calcium response to the addition of the 30 mM KCl stimulus was an about 117% increase over the baseline.

Data from Day 21 from cultures differentiated without Compound E in the differentiation medium and in response to the addition of the 30 mM KCl stimulus show that the NSCs provided an about 112.4% increase in calcium response over baseline. With Compound E in the differentiation medium at Day 21, the calcium response to the addition of the 30 mM KCl stimulus was an about 286% increase over the baseline.

In summary, the control culture provided an increase in signal of 23%, 37%, 72% and 112.4% for Day 4, 7, 14, and 21, respectively, while the test culture differentiated in the presence of Compound E provided an increase in signal of 57%, 128%, 116.9% and 286.6% for Day 4, 7, 14, and 21, respectively. The data demonstrate that cells differentiated in the presence of Compound E have greater excitability in response to a stimulus as compared to cells in the same medium without Compound E, demonstrating that the maturity of the neuronal cells is accelerated.

The compositions, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

Although the disclosed teachings have been described with reference to various applications, methods, and compositions, it will be appreciated that various changes and modifications can be made without departing from the teachings herein. The foregoing examples are provided to better illustrate the present teachings and are not intended to limit the scope of the teachings herein. Certain aspects of the present teachings can be further understood in light of the following claims.

What is claimed is:

1. A method for accelerating differentiation of at least one neural stem cell to at least one neuronal cell and concomitantly retarding neural stem cell proliferation, comprising:
    culturing the at least one neural stem cell in a differentiation medium for a time and under conditions to form the at least one neuronal cell,
    wherein the differentiation medium comprises a serum-free neural stem cell culture medium, and a serum-free supplement comprising at least one gamma secretase inhibitor wherein a differentiation signal of the at least one neuronal cell is greater by at least 100% at Day 7 of differentiation as compared to the differentiation signal of at least one neural stem cell at Day 7 of culturing in the differentiation medium lacking the at least one gamma secretase inhibitor.

2. The method of claim 1, wherein the at least one neural stem cell is derived from an induced pluripotent stem cell.

3. The method of claim 1, wherein the at least one neural stem cell is derived from an embryonic stem cell.

4. The method of claim 1 wherein the at least one neural stem cell is a SOX1 positive neural stem cell and the at least one neuronal cell is a MAP2 positive neuronal cell.

5. The method of claim 1, wherein the serum-free supplement of the differentiation medium comprises a gamma secretase inhibitor selected from the group consisting of Compound E, YO-01027, LY411575, MK-0752, a salt thereof, and a combination thereof.

6. The method of claim 5, wherein the serum-free supplement of the differentiation medium comprises a gamma secretase inhibitor selected from the group consisting of Compound E, YO-01027, LY411575, a salt thereof, and a combination thereof.

7. The method of claim 5, wherein the gamma secretase inhibitor is present in the differentiation medium at a concentration of 0.1 micromolar to 40 micromolar.

8. The method of claim 6, wherein the gamma secretase inhibitor is present in the differentiation medium at a concentration of 0.2 micromolar to 10 micromolar.

9. The method of claim 6, wherein the gamma secretase inhibitor is present in the differentiation medium at a concentration of 0.2 micromolar to 2.0 micromolar.

10. The method of claim 1 wherein the at least one neuronal cell is maintained in culture for at least a period of five weeks.

11. The method of claim 1, wherein the gamma secretase inhibitor is present in the differentiation medium at a concentration of up to 2.0 micromolar.

12. The method of claim 1, wherein the gamma secretase inhibitor is other than N-[N-(3,5-difluorophenacetyl-L-alanyl)]-S-phenylglycine t-butyl ester (DAPT).

* * * * *